United States Patent [19]

Berger

[11] Patent Number: 4,798,895

[45] Date of Patent: Jan. 17, 1989

[54] PROCESS FOR PREPARING LEVOMEPROMAZINE HYDROGEN MALEATE

[75] Inventor: Christian Berger, Ecully, France

[73] Assignee: Rhone-Poulenc Sante, Courbevoie, France

[21] Appl. No.: 66,010

[22] Filed: Jun. 24, 1987

[30] Foreign Application Priority Data

Jun. 26, 1986 [FR] France ................... 8609261

[51] Int. Cl.⁴ .......................................... C07D 279/28
[52] U.S. Cl. .......................................... 544/41
[58] Field of Search .......................................... 544/41

[56] References Cited

PUBLICATIONS

Gyogyszer, Chemical Abstracts, vol. 63 (1965) 13279b.
Pataki et al., Chemical Abstracts, vol. 72 (1970) 132,762w.
Wrotek et al., Chemical Abstracts, vol. 80 (1974) 3541q.
Jakfalvi et al., Chemical Abstracts, vol. 102 (1985) 203977w.
Jacques et al., Enantiomers, Racemates and Resolutions, Wiley-Interscience, New York (1981) pp. 72, 73 & 256.

Primary Examiner—Richard L. Raymond
Attorney, Agent, or Firm—Stevens, Davis, Miller & Mosher

[57] ABSTRACT

Levomepromazine hydrogen maleate is prepared by resolving ($\pm$)-10-(3-dimethylamino-2-methylpropyl)-2-methoxyphenothiazine with ($-$)-di(p-toluoyl)-L-tartaric acid to produce the neutral salt of the dextrorotatory base and then adding maleic acid to the mother liquors to precipitate the levomepromazine hydrogen maleate.

3 Claims, No Drawings

PROCESS FOR PREPARING LEVOMEPROMAZINE HYDROGEN MALEATE

The present invention relates to the preparation of levomepromazine hydrogen maleate from (±)-10-(3-dimethylamino-2-methylpropyl) -2-methoxyphenothiazine.

Levomepromazine or (−)-10-(3-dimethylamino-2-methylpropyl) -2-methoxyphenothiazine is a therapeutic agent which is especially useful as a tranquillizer, neuroleptic and analgesic.

It is known to prepare levomepromazine by resolution of (±)-10-(3-dimethylamino-2-methylpropyl)-2-methoxyphenothiazine with various resolving agents, e.g. tartaric acid (Hungarian Patent HU 32,813, Chem. Abstr. 102 203977 w; Hungarian Patent HU 157,158, Chem. Abstr. 72 132762 w) or dibenzoyl-D-tartaric acid (Hungarian Patent HU 152,208, Chem. Abstr. 63 13279 b), or with (−)-O-diacetyltartaramic acid (Polish Patent POL 66,636, Chem. Abstr. 80 3541 q). However, these processes do not always lead to satisfactory yields, or else they require the use of large amounts of resolving agent which may sometimes be obtainable only with difficulty.

It has now been found, and this forms the subject of the present invention, that levomepromazine hydrogen maleate can be obtained in good yield from (±)-10-(3-dimethylamino-2-methylpropyl)-2-methoxyphenothiazine (racemic base), by a process which comprises resolving (±)-10-(3-dimethylamino-2-methylpropyl)-2-methoxyphenothiazine with (−)-di(p-toluoyl)-L-tartaric acid to produce the neutral salt of (−)-di(p-toluoyl)tartaric acid and (+) -10-(3-dimethylamino-2-methylpropyl)-2-methoxyphenothiazine and mother liquors containing (−)-10-(3-dimethylamino-2-methylpropyl) -2-methoxy-phenothiazine, and then precipitating levomepromazine hydrogen maleate from the mother liquors by the action of maleic acid, and, optionally, isolating the unresolved racemic base and/or regenerating the (−)-di(p-toluoyl)-L-tartaric acid.

The process of the present invention for the resolution of (±)-10-(3-dimethylamino-2-methylpropyl)-2-methoxyphenothiazine may thus be performed in the following four stages:

(1) Crystallization of the neutral salt of di(p-toluoyl)-tartaric acid and the dextrorotatory base, (2) crystallization of the acid maleate of the laevorotatory base (levomepromazine hydrogen maleate), (3) isolation of the remaining racemic base, and (4) recovery of the di(p-toluoyl)tartaric acid for the purpose of recycling. Stages 3 and 4 are optional but preferred for economy of operation.

In general, the neutral salt of di(p-toluoyl)tartaric acid with the dextrorotatory base may be obtained by gradually cooling a hot (approximately 60° C), stirred solution of a mixture of (±)-10-(3-dimethylamino-2-methylpropyl) -2-methoxyphenothiazine and (−)-di(p-toluoyl)-L-tartaric acid in an organic solvent such as ethanol, in which the neutral salt of the dextrorotatory base is only slightly soluble or insoluble at a temperature in the region of 20° C, down to a temperature in the region of 20° C, after seeding the crystallization with a few crystals of the neutral salt of (−)-di(p-toluoyl)tartaric acid with the dextrorotatory base. The crystallization of the neutral salt of (−)-di(p-toluoyl)tartaric acid with the dextrorotatory base is generally complete after about 4 hours. Preferably, 0.25 to 0.5 mole of (−)-di(p-toluoyl) -L-tartaric acid is used per mole of racemic base employed, optionally in the presence of formic acid.

The amount of solvent is that which is sufficient for dissolving the mixture of racemic base and resolving agent in the hot state.

In general, the levomepromazine hydrogen maleate may be obtained by adding, to the filtrate originating from the separation and the washing of the neutral salt of the dextrorotatory base, a sufficient amount of maleic acid dissolved in the same solvent. The levomepromazine hydrogen maleate which precipitates is separated by filtration.

According to a feature of the invention, the racemic base which has not been resolved can be recovered by concentration followed by alkalinization, e.g. with aqueous sodium carbonate solution, of the mother liquors of crystallization of the levomepromazine hydrogen maleate, followed by extraction with a suitable solvent.

In addition, the (−)-di(p-toluoyl)-L-tartaric acid used as a resolving agent, which is present in the neutral salt of the dextrorotatory base and in the alkaline washing liquors originating from the isolation of the unresolved racemic base, can be recovered and recycled.

For example, the dextrorotatory base may be displaced from its salt by the action of a base and the (−)-di(p-toluoyl)-L-tartaric acid is obtained after acidification of the basic solution thereof. It is generally possible to recover more than 80% of the (−)-di (p-toluoyl)-L-tartaric acid employed.

The process of the present invention makes it possible to prepare levomepromazine hydrogen maleate from the racemic base in yields which are generally greater than 85%, using only a relatively small amount of resolving agent.

The Examples which follow illustrate the invention.

EAMPLE 1

(a) (±)-10-(3 Dimethylamino-2-methylpropyl)-2-methoxyphenothiazine (16.5 g; 0.05 mole), (-)-di(p-toluoyl)-L-tartaric acid monohydrate (10.15 g; 0.025 mole) and ethanol (75 cc) are introduced into a 250-cc three-necked round-bottomed flask equipped with a mechanical stirrer, a condenser and a nitrogen inlet. The stirred mixture is heated to 60° C. until a homogeneous solution is obtained. The mixture is cooled to 50° C. and crystallization is then seeded by adding a few crystals of the neutral salt of (−)-di(p-toluoyl)tartaric acid and the dextrorotatory base. While stirring is maintained, the mixture is kept for 1 hour at 50° C., cooled to 20° C. in the course of 2 hours, and maintained at 20° C. for 1 hour. The crystals obtained are separated by filtration, washed with ethanol (2×30 cc) and then dried. The neutral salt (12.99 g) of (−)-di(p-toluoyl)tartaric acid and dextrorotatory 10-(3-dimethylamino-2-methylpropyl) -2-methoxyphenothiazine is thereby obtained.

(b) A solution of maleic acid (2.94 g; 0.025 mole) in ethanol (11 cc) is added to the filtrate and to the washings of the crystals of the neutral salt obtained above. Crystals form spontaneously. The mixture is maintained for 2 hours with stirring at a temperature in the region of 20° C., and then for 18 hours at +4° C. After filtration, levomepromazine hydrogen maleate (9.76 g) is obtained in an 88% yield, its rotatory power being:

$[\alpha]_d^{20} = -7.7°$ C. (c=5, dimethylformamide)

The base liberated from an aliquot portion has a rotatory power of:

$[\alpha]_D^{20} = -15.15°$ (c=5, chloroform).

(c) The mother liquors of crystallization of the levomepromazine hydrogen maleate are concentrated to dryness under reduced pressure. The residue is taken up with methylene chloride (50 cc) and a solution of sodium carbonate (6 g) in water (60 cc) is then added. The mixture is stirred for 1 hour. The aqueous phase which is separated by decantation is washed with methylene chloride (10 cc). The organic phase is washed with water (50 cc) and then dried over sodium sulphate. After filtration and concentration under reduced pressure, (±)-10-(-3-di-methylamino-2-methylpropyl) -2-methoxyphenothiazine (1.64 g) is obtained.

(d) The neutral salt (12.99 g) of (−)-di(p-toluoyl)tartaric acid and dextrorotatory 10-(3-dimethylamino-2-methylpropyl) -2-methoxyphenothiazine is dissolved in methylene chloride (50 cc). Water (70 cc) is added and the pH adjusted to 11 by adding N sodium hydroxide solution (27.3 cc). The methylene chloride phase is separated by decantation and dried over sodium sulphate. After filtration and concentration under reduced pressure, (+)-10-(3-dimethylamino-2-methylpropyl)-2-methoxyphenothiazine (7.53 g) is obtained, its rotatory power being:

$[\alpha]_D^{20} = +15.8°$ (c=5, chloroform)

The aqueous phase (pH 11) and the washing liquors originating from the isolation of the racemic base are combined. Ethyl acetate (100 cc) is added and the pH adjusted to 2 by adding 2N hydrochloric acid (69.3 cc). The organic phase is separated by decantation and then dried over sodium sulphate. After filtration and concentration to dryness under reduced pressure, (-)-di(p-toluoyl)-L-tartaric acid (8.75 g; 86% yield) is obtained, its rotatory power being:

$[\alpha]_D^{20} = -122.8°$ (c=1, ethanol).

EXAMPLE 2

(a) (±)-10-(3-Dimethylamino-2-methylpropyl)-2-methoxyphenothiazine (6.57 g; 0.02 mole), (−)-di(p-toluoyl)-L-tartaric acid monohydrate (2.09 g), 98% strength formic acid (0.38 cc), and ethanol (30 cc) are introduced into a 100-cc three-necked round-bottomed flask equipped with a mechanical stirrer, a condenser and a nitrogen inlet. The stirred mixture is heated to 60° C. until a homogeneous medium is obtained. The mixture is cooled to 50° C. and a few orystals of neutral salt of (−)-di(p-toluoyl)tartaric acid and dextrorotatory base are th:n added.

Ihe temperature is kept for 1 hour at 50° C and the mixture is then cooled from 50° C. to 20° C. in the course of 2 hours. The mixture is maintained for 1 hour at 20° C. with stirring. The crystals obtained are separated by filtration, washed with ethanol (2×12 cc) and dried. The neutral salt (3.98 g) of (−)-di(p-toluoyl)tartaric acid and dextrorotatory 10-(3-dimethylamino-2-methylpropyl)-2-methoxyphenothiazine is thereby obtained, its rotatory power being:

$[\alpha]_D^{20} = +16.6°$ (c=5, chloroform).

(b) Maleic acid (1.16 g) is added to the filtrate and the washings of the crystals of the neutral salt obtained above. Crystals develop spontaneously at a temperature in the region of 20° C. The mixture is stirred for 2 hours at a temperature in the region of 20° C. and then for 18 hours at 4° C. After filtration, levomepromazine hydrogen maleate (3.52 g) is obtained.

The base liberated from an aliquot portion has a rotatory power of:

$[\alpha]_D^{20} = -13.7°$ (c=5, chloroform).

I claim:

1. A process for preparing levomepromazine hydrogen maleate from (±)-10-(3-dimethylamino-2-methylpropyl)-2-methoxyphenothiazine, which comprises resolving (±)-10-(3-dimethylamino-2-methylpropyl)-2-methoxyphenothiazine with (−)-di(p-toluoyl)-L-tartaric acid using 0.25 to 0.5 mole of (−)-di(p-toluoyl)-L-tartaric acid per mole of (±)-10-(3-dimethylamino-2-methylpropyl) -2-methoxy-phenothiazine to produce the neutral salt of (−)-di(p-toluoyl) tartaric acid and (±)-10-(3-dimethylamino-2-methylpropyl) -2-methoxyphenothiazine and mother liquors containing (−)-10-(3-dimethylamino-2-methylpropyl)-2-methoxyphenothiazine, and the precipitating levomepromazine hydrogen maleate from the mother liquors by the action of maleic acid, and, optionally, isolating the unresolved racemic base and/or regenerating the (−)-di(p-toluoyl)-L-tartaric acid.

2. Process according to claim 1, in which the said resolution is carried out in ethanol in sufficient amount to dissolve in the hot state the (±)-10-(3-dimethylamino -2-methylpropyl)-2-methoxyphenothiazine and (−)-di(p-toluoyl)-L-tartaric acid.

3. Process according to claim 5, in which one mole of maleic acid is used per mole of the racemic base resolved.

* * * * *